United States Patent [19]

Brezin et al.

[11] Patent Number: 5,095,094
[45] Date of Patent: Mar. 10, 1992

[54] A43 KDA ANTIGENIC PROTEIN OF BORDETELLA RECOGNIZED BY POLYCLONAL ANTIBODIES TO ADENYLATE CYCLASE BUT DEVOID OF CALMODULIN-ACTIVATABLE ADENYLATE CYCLASE ACTIVITY

[75] Inventors: Colette Brezin; Hoàng-Oanh Nghiêm, both of Paris; Jean Luc Boucaud, Cours-La-Ville; Jean M. Alonso, Montigny le Bretonneux, all of France

[73] Assignees: Institut Pasteur; Institut National de la Sante et de la Recherche Medicale, both of Paris, France

[21] Appl. No.: 483,298

[22] Filed: Feb. 20, 1990

Related U.S. Application Data

[63] Continuation of Ser. No. 340,550, Apr. 19, 1989, abandoned.

[30] Foreign Application Priority Data

Apr. 19, 1988 [GB] United Kingdom ............... 88400950

[51] Int. Cl.$^5$ ...................... C07K 15/04; C07K 15/14
[52] U.S. Cl. ..................... 530/350; 530/395; 530/806; 424/92; 435/232
[58] Field of Search .................. 530/350, 395; 424/92; 435/232

[56] References Cited

U.S. PATENT DOCUMENTS 4,279,884 7/1981 Bradwell et al. ............... 424/1
4,427,653 1/1984 Springer ..................... 424/85.8

FOREIGN PATENT DOCUMENTS 0162639 11/1985 European Pat. Off. .

OTHER PUBLICATIONS

Development in Biological Standardization, 1985, pp. 27–42, P. Novotny et al.: "Bordetella Adenylate Cyclase: A Genus Specific Protective Antigen and Virulence Factor".
Journal of Infections Diseases, vol. 3, 1977, pp. S216–S219; E. L. Hewlett et al.: "Adenyl Cyclase in Bordetella Pertussis Vaccines".
Infection and Immunity, vol. 50, No. 1, Oct. 1985, pp. 199–206, American Society for Microbiology; P. Novotny et al.: "Adenylate Cyclase Activity of a 68.000-Molecular-Weight Protein Isolated from the Outer Membrane of Bordetella bronchiseptica".
Chemical Abstracts, vol. 105, No. 21, 24th Nov. 1986, p. 311, Abstract No. 186455s, Columbus, Ohio, US; D. Ladant et al.: "Bordetella Pertussis Adenylate Cyclase. Purification Characterization, and Radioimmunoassay" & J. Biol. Chem. 1986, 261(34), 16264–16269.
Ladant, D. 1988 J. Biol. Chem. 263(6):2612–2618.
Glaser et al. 1989, The EMBO Journal 8(3):967–972.

Primary Examiner—Margaret Moskowitz
Assistant Examiner—Keith C. Furman
Attorney, Agent, or Firm—Finnegan, Henderson, Farabow, Garrett & Dunner

[57] ABSTRACT

The proteins of the invention are specifically recognized by polyclonal anti-AC antibodies raised against purified AC preparations, devoid of adenylate cyclase CaM-activable activity and devoid of affinity for CaM.

1 Claim, 2 Drawing Sheets

Figures 2-1, 2-2:
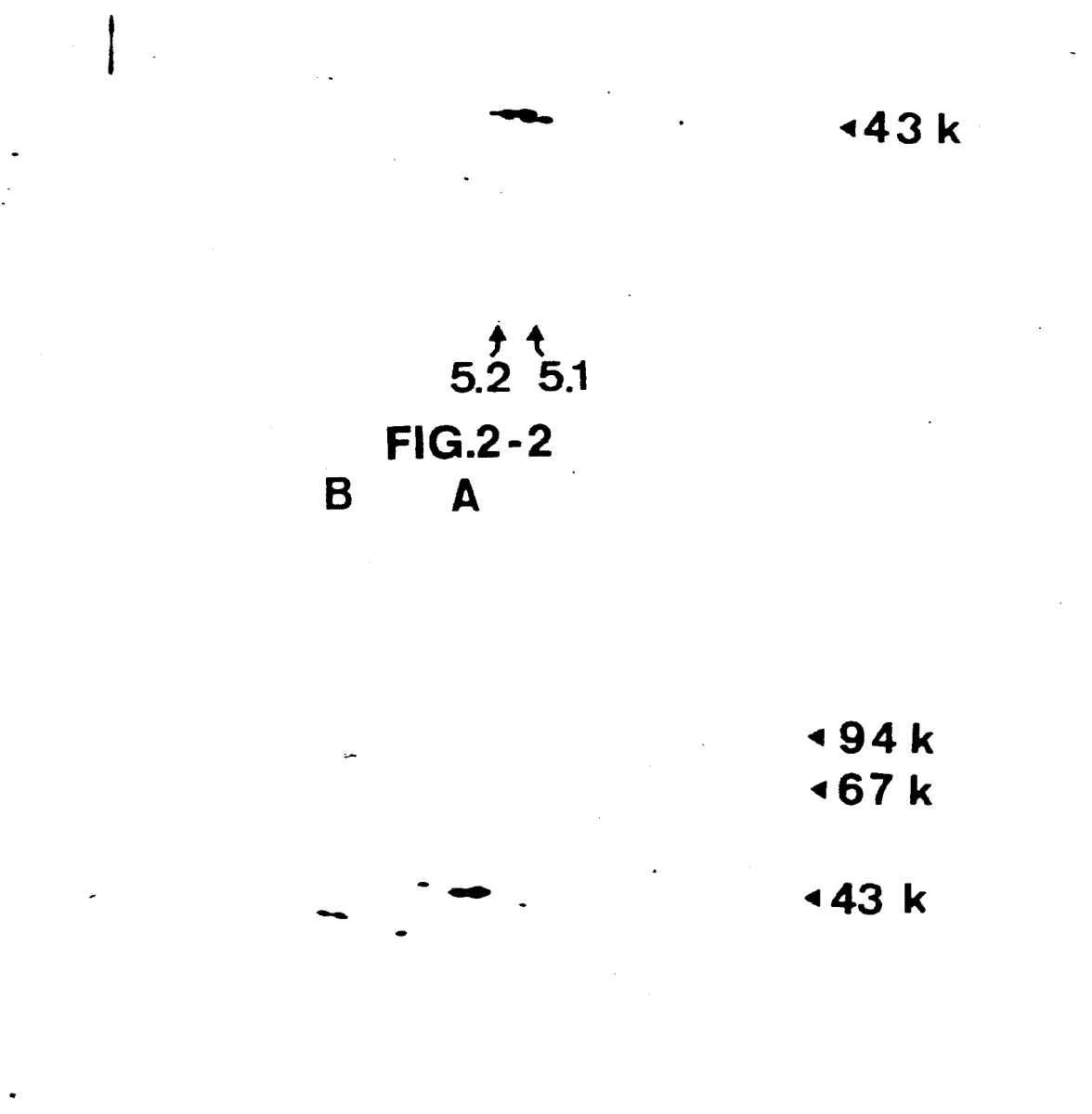

A43 KDA ANTIGENIC PROTEIN OF BORDETELLA RECOGNIZED BY POLYCLONAL ANTIBODIES TO ADENYLATE CYCLASE BUT DEVOID OF CALMODULIN-ACTIVATABLE ADENYLATE CYCLASE ACTIVITY

This application is a continuation of application Ser. No. 340,550, filed Apr. 19, 1989, abandoned.

BACKGROUND OF THE INVENTION

*Bordetella pertussis* the causative agent of whooping cough secretes or releases during exponential growth, a highly active adenylate cyclase (AC) that has been demonstrated to be a major toxin, as well as an immunoprotective antigen in experimental infection of mice.

This enzyme shares in common with the secreted adenylate cyclase (edema factor) of *Bacillus anthracis*, the anthrax bacillus, and with the eucaryotic adenylate cyclase, the property of being activable by a eucaryotic protein, calmodulin (CaM). Experiments with enriched preparations of AC have provided some evidence that this enzyme is able to invade various eucaroytoc cells and subsequently, to promote a rapid, non regulated, increase of intracellular cAMP. This cAMP-mediated cytopathic effect is clearly distinguished from the deregulation of eucaryotic adenylate cyclase produced by another toxin of *B.pertussis*, the pertussis toxin.

It is known since its discovery that *B. pertussis* undergoes spontaneous phase variations associated with loss of expression of several phenotypical characteristics including AC activity. However it is not clear whether these phenotypical changes result from the lack of expression (synthesis, export and/or release) of the molecule or its loss of catalytic activity.

By using a set of anti-AC antibodies, the inventors have checked the expression of AC antigen in virulent or avirulent *B.pertussis* variants and corrected this immunological detection with enzymatic activity.

By carrying out their work, they have found in virulent and avirulent crude bacterial extracts, a protein devoid of catalytic adenylate cyclase activity, but having valuable antigenic properties.

It is then an object of the invention to provide a new protein useful as an immunoprotective antigen in human and animals particularly against Bordetella infections and toxic processes by pathogenic bacteria.

SUMMARY OF THE INVENTION

The protein of the invention is characterized by the following features:

- its molecular weight (Mr) is of about 43±4.3 kDa,
- its isoelectric point (pI) is of 5.7–6.1, particularly of 5.9,
- it is specifically recognized by polyclonal anti-AC antibodies raised against purified active AC preparations,
- it is devoid of CaM activatible adenylate cyclase activity,
- it is devoid of affinity for CaM.

DESCRIPTION OF PREFERRED EMBODIMENTS

The molecular weight (molecular range Mr) was determined using ovalbumin as standard. The isoelectric point pI corresponds to the electrophoretic migration as determined according to the method of O'Farrell et al. in reference (6) (the articles to which it is referred therein are given at the end of the description).

It is remarkable that such a protein which is inactive with respect to catalytic adenylate cyclase enzymatic activity, has a structural antigenic analogy with the active AC of Bordetellae, especially *B.pertussis*.

According to the invention, it has thus been found that the inactive and active adenylate cyclases have at least one common epitope.

The terms "inactive" and "active", as used in the specification, refer to adenylate cyclase enzymatic activity.

This protein also exists in a higher molecular weight form, of about 90 kDa, having the same properties, particularly the same pI as the lower molecular weight protein, suggesting that it might be a dimer.

The protein of the invention is obtainable from virulent bacteria and variants thereof which express active AC, more particularly from pathogenic bacteria whose AC is capable of interfering with the AC of eucaryotic cells. Accordingly, both active and inactive forms exist in said bacteria. Only the active form is secreted. However *B.avium* cultures only contain the inactive form.

Said protein is obtainable from Bordetellae. Bordetellae used to obtain the protein of the invention are those responsible for respiratory diseases in vertebrates such as *Bordetellae pertussis* and *Bordetellae parapertussis* in man, and *Bordetellae bronchiseptica* and *Bordetellae avium* in animals.

Cross-reacting proteins, but having molecular weight different from that of said protein, can also be found in *Bacillus anthracis*, Yersiniae, and Pasteurellae.

Said antigenic protein and cross-reacting antigens are also obtainable from avirulent variants in which no adenylate cyclase enzymatic activity has ever been found.

Variants of said virulent and avirulent strains can be used according to the invention inasmuch as they produce antigenic molecules with cross-reactivity.

The bacterial extracts useful for the extraction of the protein and molecules with cross-reactivity of the invention are obtained for example by treating bacterial cells expressing AC with urea and by recovering the protein after centrifugation of the supernatant. Any other kind of bacterial lysis or molecular cloning can be used as a source for the protein.

The proteins of the invention can be purified, through immunoaffinity with specific antibodies against native adenylate cyclase of *B.pertussis* and *B.parapertussis*.

The study of infections produced by bacteria synthetizing proteins of the invention in a mouse model enables identification of their antigenic properties.

Said proteins indeed appear capable of inducing protection, since specific antibodies can passively provide full protection against intranasal challenge with *B.pertussis* or *B.parapertussis*.

The toxicology assays carried out in bacteria producing these antigens having shown the absence of toxicity thereof when administered by the intranasal or even parenteral route to mouse, the purified proteins can be advantageously used for the preparation of vaccinating principles, provided that they do not exhibit cross-reactivity with the proteins of the treated eucaryotes.

The vaccines of the invention are thus characterized in that they are molecular vaccines containing said antigenic proteins in combination with a pharmaceutical carrier.

The usual does and pharmaceutical forms are used.

In the vaccine compositions of the invention, the antigenic proteins may be associated with filamentous hemaglutin (FHA) in the same inoculum or not. FHA will then be administered at the same time as the adenylate cyclase or at different times. FHA preparations are advantageously obtained using the method, for example, of Sato et al. in Infect. Immun, 1983, 41, 313–320 or Imaizumi et al., Journal of Microbiol. Methods, 2, 334–347 (1984).

In another embodiment, the antigenic proteins may be associated with purified AC preparations such as disclosed in FR patent application 8615963 filed Nov. 17, 1986, in the name of the applicants, and optionally with FHA.

Advantageously, the vaccine compositions of the invention particularly prevent the infection caused by Bordetellae.

The vaccination is advantageously carried out by intranasal, oral or parenteral route.

An active immunization against B.pertussis intranasal infection is thus obtained with whole cell vaccines prepared from avirulent AC B.pertussis.

The invention also relates to polyclonal antibodies directed against said proteins as new products.

These antibodies are produced, for example, by immunizing animals such as rabbits or mice by means of the proteins in question and by recovery of the antisera containing the antibodies and then by recovery of the antibodies themselves by standard methods.

The invention also relates to monoclonal antibodies such as those obtained by fusion of a mouse myeloma with spleen lymphocytes derived from mice immunized with said purified proteins. These preparations of monoclonal immunoglobulins are characterized in that they specifically recognize an epitope of the purified proteins which leads to the induction of the synthesis of protective antibodies.

In an advantageous manner, the antibodies according to the invention exercise an immunoprotective effect against the pathogenic effects of the above bacteria.

Other characteristics and advantages of the invention will be given in the following example, with reference to the figures, wherein:

BRIEF DESCRIPTION OF THE DRAWINGS

In FIG. 1A polyclonal antibodies raised against purified AC preparations were used. In FIG. 1B monoclonal antibodies raised against the purified AC preparations were used;

FIG. 2I and 2II represent immunoblots obtained from two-dimensional gel electrophoresis of purified AC or AC extracts with anti-AC antibodies.

MATERIALS AND METHODS

Figure 1:
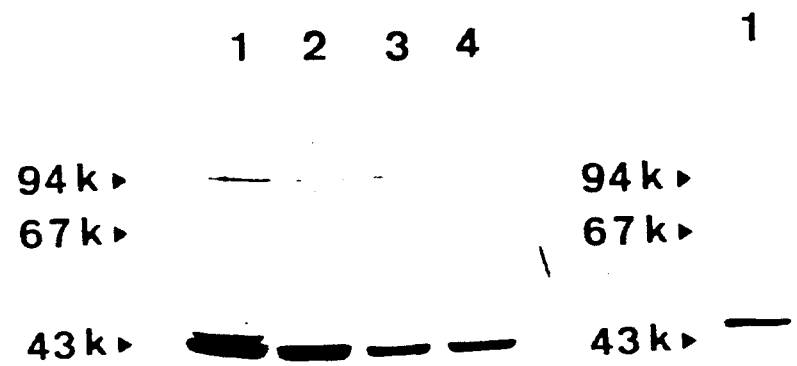
FIG. 1 represents immunoblots of extracts from virulent or non-virulent B.pertussis with different anti-AC antibodies.

The materials and methods used in the example are the following:

BACTERIAL STRAINS: B.pertussis 18323 (type strain ATCC 9797) isogenic $AC^{30}$ (in terms of adenylate cyclase enzymatic activity) or $AC^-$ variants were selected from cultures on Bordet-Gengou blood agar plates (1).

Calmodulin-affinity purification of AC from periplasmic and extracellular extracts, radioimmunoassay (RIA) and dosage of enzymatic activity, were performed as described in (2), (3) and (4) respectively.

A control RIA was assayed with concentrated solution of bovine serium albumin (BSA) in order to check for a non-specific inhibition by a concentration protein preparation.

Mice polyclonal and monoclonal antibodies raised against the affinity purified calmodulin molecules were described in (2).

SDS-PAGE: was performed in 7.5% acrylamide as described by Laemmli in (5).

TWO-DIMENSIONAL ISOELECTRIC FOCUSING and SDS-PAGE electrophoresis was carried out according to O'Farrell (6). Ampholine pH 3–10 (Pharmacia) and pH 4–9 (Servalyte) were used.

The protein concentration was routinely determined by Schnaffer method (7) with BSA as standard.

WESTERN-BLOT ANALYSIS: After SDS-PAGE, proteins were transferred to nitrocellulose by the Towbin method (8). After transfer, the nitrocellulose was saturated with 5% milk powder (Régilait écrémé France-Lait) in 50 mM Tris HCl, pH 8, 150 mM (buffer A) and incubated with mouse antibodies diluted in milk buffer A. After washing with buffer A two kinds of development procedures were performed: either with horseradish peroxydase conjugated goat anti-mouse IgG (Biosys France) revealed by 3.3 diaminobenzidine (500 g/ml) 0.03% $H_2O_2$, 100 mM Tris HCl pH7.6; either with phosphatase conjugated antibodies (Biosys France).

1. Immunoblots of bacterial periplasmic extracts with anti-AC antibodies.

Immunoblots of bacterial periplasmic extracts from virulent of non-virulent B.pertussis (SDS-PAGE with 7.5% acrylamide) with different anti-AC antibodies were compared.

The extracts were obtained by extracting $AC^{30}$ and $AC^-$ variants of B.pertussis 18328 such as obtained by (3).

These extracts were reacted with:

A/polyclonal antibodies raised against purified AC preparations.

B/monoclonal antibodies against said purified AC preparations.

The purified AC preparations are advantageously those disclosed in FR patent application (reference 2) in name of the applicants.

Such preparations are characterized in that they posses a high degree of purity and are virtually totally devoid of contaminating bacterial substances, in particular pertussis toxins, lipopolysaccharide (or LPS) and filamentous hemagglutinin (or FHA). The AC is thus available in a homogeneous form, sedimenting with a S coefficient equal to 3.6 in a sucrose density gradient, and exists in two structurally related molecular forms. of 45 and 43 kDa, respectively.

According to another aspect the preparations of AC are characterized in that they possess an enzymatic activity which may attain and even exceed 1600 micromoles of cAMP $min^{-1}$. $mg^{-1}$ The purified AC preparations are obtainable by placing the contact a previously concentrated supernatant of bacterial cultures expressing adenylate cyclase or an extract of these bacteria with calmodulin.

The polyclonal antibodies are produced, for example, by immunizing animals such as the rabbits or mice by means of the AC preparations where question in the AC is free or in the form of a complex with eucaryotic proteins, in particular with calmodulin, and by recovery of the antisera containing the antibodies and then of the antibodies themselves by standard methods.

The monoclonal antibodies are obtainable by fusion of a mouse myeloma with spleen lymphocytes derived from mice immunized with purified adenyl cyclase.

Monoclonal antibodies (8-25) are particularly used. They immunopreprecipitate a triplet of 50, 45 and 43 kDa as well as a protein with a molecular weight higher than 100 kDa in crude extracts and preparations of the enzyme purified from bacterial cells.

The hybridoma strain producing the monoclonal antibodies was deposited with the Collection Nationale de Cultures de Microorganismes (CNCM) under the No. I-610 on Oct. 9, 1986.

RESULTS

The immunoblots obtained are reported in FIG. 1, wherein in parts A and B corresponding to the above reactions, lanes 1 and 3 correspond to the reaction with the crude extracts of $AC^+$ and $AC^-$ variants respectively and lanes 2 and 4 to the same extracts after depletion of the calmodulin binding protein. AC activity of (1)=2,000 units, (2)=100 units, (3) and (4) is less than one unit.

FIG. 1 shows that different patterns of recognition by the different antibodies are exhibited by these extracts. In the $AC^+$ bacterial urea extracts (lane 1), three bands at respectively Mr 43, 45 and 90 kDa, were seen in Western blot with the polyclonal antibodies raised against the pure homogenous 43–45 kDa AC complex. After depletion of the calmodulin binding molecule from the crude $AC^+$ urea extract the band of 45 kDa disappeared.

Western blot analysis of the $AC^+$ urea extract with the monoclonal anti-AC antibody showed that only the calmodulin binding molecule was recognized by this antibody.

This antigen was not detected in the $AC^-$ crude urea extracts, by polyclonal or monoclonal anti-AC antibodies (lanes 2 and 4).

Dosages of activity of these different extracts showed that disappearance of the 45 kDa band correlated with loss of significant AC activity. In the urea extract $AC^+$ activity was around 1,000 to 2,500 units (one unit corresponds to one nanomole of cAMP formed per minute at 30° C., pH 8), and only 20 to 40 units after passing this crude extract through the CaM-affinity column. The CaM-affinity eluted molecule was recognized both by poly or monoclonal antibodies, had a cyclase activity of 8,000 to 20,000 units per ml and an apparent Mr of 45 kDa.

2. Immunoblots on two-dimensional polyacrylamide gel:

Immunoblots on two-dimensional polyacrylamide gel were performed, the gel containing:

I) CaM purified AC (detected by nonoclonal antibodies) (the same image is obtained with polyclonal antibodies) pi=5.1, Mr 45 kDa, IgG was reacted with peroxydase labelled rabbit antimouse. The immune complex was detected with diethyl-amino-benzidine (DAB) revelation;

II) Crude urea extract of a virulent variant (same as in FIG. 1).

The resulting immunoblots are given in FIGS. 2I and 2II respectively. In these figures, A and B correspond to:

A: the first detection with monoclonal antibodies, IgG peroxydase, DAB,

B: the second detection with antimouse phosphatase labelled polyclonal antibodies (crude extract revealed only by polyclonal antibodies give the same picture as A plus B).

A purified AC was detected in FIG. 2I at Mr 45 kDa with an isoelectric point (pI) of 5.2-5.1 by both monoclonal and polyclonal antibodies. This pI value was confirmed from $^{125}I$ labelling of the CaM affinity purified AC detected by autoradiograms.

The $AC^+$ urea extract (FIG. 2II) reveals three kinds of molecules when detected with the polyclonal antibodies, according to their Mr and pI: at 45 kDa with a pI of 5.2-5.1 and two at 43 kDa and at 90 kDa respectively with a pI of 6-5.8. The two bands at pI 6-5.8 were recognized in the flowthrough of a CaM affinity column.

The monoclonal antibody only revealed a protein of 45 kDa in the $AC^+$ urea extract and no longer revealed any protein after the $AC^+$ urea extract had been passed through the CaM affinity column.

SPECIFIC PURIFICATION OF ANTIBODIES (9)

The polyclonal anti-AC antibodies were incubated with strips of nitrocellulose to which antigens had been transferred by Western blotting. The strips were cut, in order to have an antigen preparation restricted to 43 kDa proteins. The 3 mm large strip was chosen from previous immunoblotting on a control sampling slice of each western blot revealing the 43 kDa antigen by anti-AC polyclonal antibodies. Elution of antibodies fixed to nitrocellulose strips was achieved with HCl glycine buffer pH 2.8 after 2 min., 5 min. or 10 min. of incubation followed by immediate neutralisation with phosphate buffer. These antibodies were tested for specificity against various antigen preparations. These antibodies reacting with the homologous 43 kDa molecule and cross-reacted with the CaM-affinity purified 45 kDa AC.

RADIOIMMUNOASSAY

In the radioimmunoassay, the inhibition of fixation of $^{125}I$ labelled CaM-binding AC on polyclonal antibodies was assayed with B.pertussis extracts. The purified AC and urea extract of $AC^+$ bacteria or culture supernatant inhibited fixation in a similar fashion. The $AC^-$ supernatant or urea extract weakly inhibited the fixation of anti-AC antibodies to AC.

The percentage of inhibition by various extracts of proteins, varied as a function of the relative protein concentration of the sample.

IMMUNOPROTECTIVE EFFECT

Heat-inactivated vaccine (80° C.) administered subcutaneously in one infection provided 50% protection.

The articles to which it is referred to in the specification are given hereinafter:

(1) Brézin, C. et al., FEMS Microbiol. Lett. 42, 75-80, (1987).

(2) FR patent application 8615963 of Nov. 17, 1986 in the names of Institut Pasteur and Inserm.

(3) Ladant, D. et al. J. Biol. Chem. 261, 16264–16269, (1986).

(4) White A. A. et al., Methods Enzymol., 38C, 41–46, (1974); such as modified by Hanoune et al., J. Biol. Chem., 252, 2039–2046, (1977).

(5) Laemmli, Nature (London), 227, 680–685, (1976).

(6) O'Farrell, J. Biol. Chem., 250, 4007–4021, (1975).

(7) Schnaffer, W. et al., Anal. Biochem., 1973, 56, 502-514, (1973).

(8) Towbin, H. Proc. Natl. Acad. Sci. U.S.A., 76, (1979)

(9) Nghiêm H. O., (1988) Journal of Immunological Methods, JIM 04806, in press (1988).

We claim:

1. A purified and isolated protein having a molecular weight of about 43±4.3 kDa as determined by sodium dodecyl sulphate polyacrylamide gel electrophoresis under reducing conditions, and a pI of 5.7-6.1, wherein said protein:
   (a) is specifically recognized by polyclonal anti-adenylate cyclase antibodies raised against purified adenylate cyclase preparations;
   (b) is devoid of calmodulin-activatable adenylate cyclase activity;
   (c) is devoid of affinity for calmodulin; and
   (d) is in a purified form essentially free of pertussis toxin, lipopolysaccharide, and filamentous hemagglutinin.

* * * * *